United States Patent
Garibaldi et al.

(10) Patent No.: US 6,315,709 B1
(45) Date of Patent: Nov. 13, 2001

(54) MAGNETIC VASCULAR DEFECT TREATMENT SYSTEM

(75) Inventors: Jeff Garibaldi, St Louis, MO (US); Bevil J. Hogg, Santa Cruz, CA (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 09/271,118

(22) Filed: Mar. 17, 1999

Related U.S. Application Data (60) Provisional application No. 60/095,710, filed on Aug. 7, 1998, and provisional application No. 60/112,251, filed on Dec. 14, 1998.

(51) Int. Cl.$^7$ .............................. A61M 37/00; A61N 2/00
(52) U.S. Cl. .............................................................. 600/12
(58) Field of Search ................................ 600/12, 9, 11, 600/433, 435, 139; 606/32; 424/9; 604/95, 96, 280, 264, 523, 19, 48

(56) References Cited

U.S. PATENT DOCUMENTS

| | | | |
|---|---|---|---|
| 4,005,699 | * | 2/1977 | Bucalo ................................. 600/12 |
| 4,331,654 | * | 5/1982 | Morris ................................. 600/12 |
| 4,849,210 | * | 7/1989 | Widder ................................. 424/9 |
| 4,863,715 | * | 9/1989 | Jacobsen et al. ...................... 424/9 |
| 5,122,136 | * | 6/1992 | Guglielmi et al. .................... 606/32 |
| 5,236,410 | | 8/1993 | Granov et al. . |
| 5,262,176 | * | 11/1993 | Palmacci et al. ..................... 600/12 |
| 5,349,957 | * | 9/1994 | Yudelson ............................... 600/12 |
| 5,702,361 | | 12/1997 | Evans et al. . |
| 5,707,335 | * | 1/1998 | Howard et al. ....................... 600/12 |
| 5,779,694 | * | 7/1998 | Howard et al. ....................... 600/12 |
| 5,855,578 | * | 1/1999 | Guglielmi et al. .................... 606/32 |
| 5,860,923 | * | 1/1999 | Lenker et al. ....................... 600/433 |

OTHER PUBLICATIONS

Alksne et al., Iron–acrylic Compound for Stereotaxic Aneurysm Thrombosis, *J. of Neurosurgery* 47:137–141 (1977).
Gaston et al., External Magnetic Guidance of Endovascular Catheters with a superconducting Magnet: Preliminary Trials, *J. Neuroradiol.* 15:137–147 (1988).

* cited by examiner

*Primary Examiner*—John P. Lacyk
*Assistant Examiner*—Brian Szmal
(74) *Attorney, Agent, or Firm*—Harness, Dickey & Pierce, P.L.C.

(57) ABSTRACT

Device and method for treating vascular defects by filling the defect with magnetically controlled devices. Vascular defects include aneurysms and arteriovenous malformations (AVMs), particularly in the head and neck of the patient. The magnetic devices fall into categories of ferro-fluids, magnetic objects and magnetic coils. Ferro-fluids consist of a magnetic particulate that is combined with a glue or polymer agent. The ferro-fluid is magnetically held and solidified, while the adhesive agent cures. Magnetic objects such as polyvinyl alcohol (PVA) coated magnetic particles can be injected into a vascular defect such as an AVM. The magnetic objects are attracted into pre-selected AVM branches by the application of a magnetic gradient. Magnetic coils are magnetically steered and held within an aneurysm to improve coil delivery. Large neck aneurysms are particularly assisted by this method, due to the need to steer the coil towards the center of the aneurysm and to hold the coils within the aneurysm. Various methods of magnetically controlling these devices are described to cover a broad range of new treatment approaches.

44 Claims, 4 Drawing Sheets

MAGNETIC VASCULAR DEFECT TREATMENT SYSTEM

CROSS-REFERENCE TO RELATED APPLICATIONS

Our co-pending applications show devices and methods useful for carrying out this invention. Co-pending U.S. Provisional Patent Applications entitled "Method and Apparatus for Magnetically Controlling Catheters in Body Lumens and Cavities" filed Aug. 7, 1998 serial No. 60/095,710 and "Open Field System for Magnetic Surgery" filed Dec. 14, 1998 Ser. No. 09/211,723 and "Articulated Magnetic Guidance System" filed Nov. 10, 1998 Ser. No. 09/189,633 and "Magnetically Controlled Fluids for Treating Aneurysms" filed Dec. 14, 1998 serial No. 60/112,251 are all incorporated by reference herein in their entirety.

FIELD OF THE INVENTION

The present invention relates generally to both a method and related apparatus for treating vascular defects such as aneurysms or arteriovenous malformations (AVMs) in a patient's vasculature. More particularly the invention is directed to a system well suited for treating vascular defects in vessels in the head and neck of a patient.

BACKGROUND OF THE INVENTION

Aneurysms are circumscribed dilations connecting directly with the lumen of a blood vessel. Aneurysms may result from acquired or congenital diseases which create a weakness in the blood vessel wall. It should be appreciated that aneurysms have a relatively turbulent flow of blood through the "neck" of the aneurysm. AVMs are inappropriately interconnected vessels that shunt blood from the arterial circulation to the venous flow. AVM defects are usually congenital. Depending on vessel size and the nature of the interconnections that make up the malformation, AVMs can also be accompanied by substantial blood flow. In both of these types of vascular defect the presence of blood flow complicates treatment.

Typically aneurysms have thin walls which are vulnerable to a sudden rupture. If an aneurysm ruptures, the resulting hemorrhage can cause death. A hemorrhage can also cause both excessive pressure on nearby tissues and a reduction of blood flow to the tissues "downstream" of the aneurysm.

Neurosurgeons have perfected certain conventional treatments for embolizing aneurysms in small vessels of the brain. The embolization process causes the aneurysm to heal in a way that removes the "pocket" from the wall of the vessel. In the most mature technique, the neurosurgeon accesses the region of the aneurysm under direct visualization through a craniotomy and places one or more aneurysm clips on the "neck" or opening of the aneurysm. This conventional open surgical approach has a high rate of success, but is highly invasive and undesirable for that reason. The risk associated with conventional approaches has encouraged the development of minimally invasive intravascular treatment approaches. Currently, the most widely used minimally invasive technique, involves placement of small coils of wire into the aneurysm. The coils are delivered transluminaly through a catheter that is navigated to the aneurysm site. Once the catheter is advanced into the neck of the aneurysm, multiple coils are released into the aneurysm. The coils dramatically reduce the blood flow through the aneurysm, which results in clotting within the aneurysm. The GDC coiling procedure can be time-consuming due to the number of coils that need to be inserted and released to fill or "pack" the aneurysm. The coiling procedures often need to be repeated because it is difficult to completely 'pack" the aneurysm with coils. In this procedure the "neck" of the aneurysm helps to retain the coils. Consequently there are a substantial number of aneurysms which cannot be treated using coils because the large neck allows the first coil to escape from the aneurysm. This common problem is seen radiographically as the first coil curving out of the aneurysm and entering the associated vessel branch. Retrieving an repositioning coils is both difficult and time consuming.

In additions to "coils", liquid or semi-liquid occlusive embolic materials have been proposed for use in treating aneurysms. These fluids include iron-acrylic compounds, as well as, a large collection of biocompatible glues and polymers. Attempts have been made to inject the occlusive materials directly into aneurysms to fill the cavity of the aneurysm. Typically this procedure uses a needle to pierce the wall of the aneurysm to place the material. There has been limited success using these fluids due to the tendency of the blood flow to pass the embolic material out of the aneurysm. This "wash out" situation presents serious complications due to the high probably of occluding the distal branches of the cerebral vasculature. Some investigators have attempted to treat aneurysms with liquids that denature proteins such as alcohol and the like. These procedures are risky as well due to the fact that the treatment occurs in a vessel with active blood flow and the denaturing process can occur in healthy tissue by accident.

The literature has reported several studies where magnetic particles are combined with other materials to serve as an embolic material. The studies have reported improved success in treating aneurysms. In one representative study, a needle surrounded by a magnet was inserted through a burr hole in the patient's head. A stereotactic frame attached to the patient's head was used to direct the needle to the dome of the aneurysm. The mixture of magnetic particles and occlusive agent was injected through the needle, across the wall of the vessel. The study revealed several defects or shortcomings including the need for a burr hole in the skull and a prolonged embolization time for the occlusive agent. Complications also resulted from rupturing the aneurysm. In the reported study the magnet remained in place in the patient's head for several days to completely embolize the aneurysm. The reported technique was unable to hold a magnetic mixture in aneurysms greater than about 1-cm in diameter.

AVMs may also be treated with embolic materials. The most frequently reported technique involves the use of very small polyvinyl alcohol particles, which are sized to occlude the smallest fistulas in the AVM. This technique involves "guess work" to prepare the right size particles that will not pass through the AVM. Also, there is limited control of the emboli, since the catheter placement and the direction of greatest blood flow dictate the delivery of the embolic particles. Visualization of the particles is problematic as well.

For these reasons it is desirable to improve treatment techniques for vascular defects such as aneurysms and AVMs.

SUMMARY

The methods and devices presented in this invention can be used to treat vascular defects such as aneurysms and AVMs as found within the body. The invention is disclosed in the context of neurovascular treatments for ease of explanation, but the context should not be taken as a limitation in the scope of the invention. For example, the invention maybe used to treat other larger arteriovenous malformations, fistulas or aneurysms elsewhere in the body.

The method of the invention involves the navigation of a catheter to a treatment site with or without the aid of an external magnetic field. Once the distal tip of the catheter is located at the treatment site, a magnetic device is delivered into the aneurysm. The magnetic device is held in position by the application of an external magnetic field.

The term magnetic device refers to two types of embolic devices and their equivalents. In each case, the device carries a magnetically active element or particle. In one embodiment, the magnetic device is a macroscopic magnetically responsive occlusion device such as a coil, the second type of magnetic device is a "ferro-fluid" which is a viscous liquid containing magnetically active particulate. In either embodiment, magnetically active material contributes to the functional properties of the device.

In general, the magnetic device may be shaped, delivered or steered by using magnetic fields or gradients. Magnetic fields align a magnetic object in the direction of the applied field, while magnetic gradients pull a magnetic object in the direction of the applied gradient. Magnetic fields and gradients can be used separately or in combination to achieve the desired effect. When used in combination, the magnetic field can be axially aligned with the gradient or transversely with the gradient. These two forms of gradients are often referred to as "axial" or "transverse," respectively. All of the various magnetic fields and gradient configurations provide unique control to the magnetic device, although for each device and procedure it is likely that one configuration will prove optimal.

In general, the externally applied magnetic field and field gradient assists in the positioning and retaining the magnetic device during the procedure. For example the applied field supplies a sufficient force to hold a large volume of ferro-fluid in the aneurysm or AVM and to steer and retain magnetically "tipped" coils in the aneurysm. A local magnetic field and gradient generated by the distal tip of the catheter can also cooperate to shape and retain the ferro-fluid or control the release of the magnetic device.

The incorporated references discuss certain imaging and navigation techniques that may be used advantageously with the devices and methods of the present invention.

BRIEF DESCRIPTION OF THE DRAWINGS

Throughout the several views of the drawings which illustrate an exemplary embodiment of the invention, like reference numerals indicate identical structure, wherein.

DETAILED DESCRIPTION

Figures 1, 2, 3, 4, 5, 6, 7:
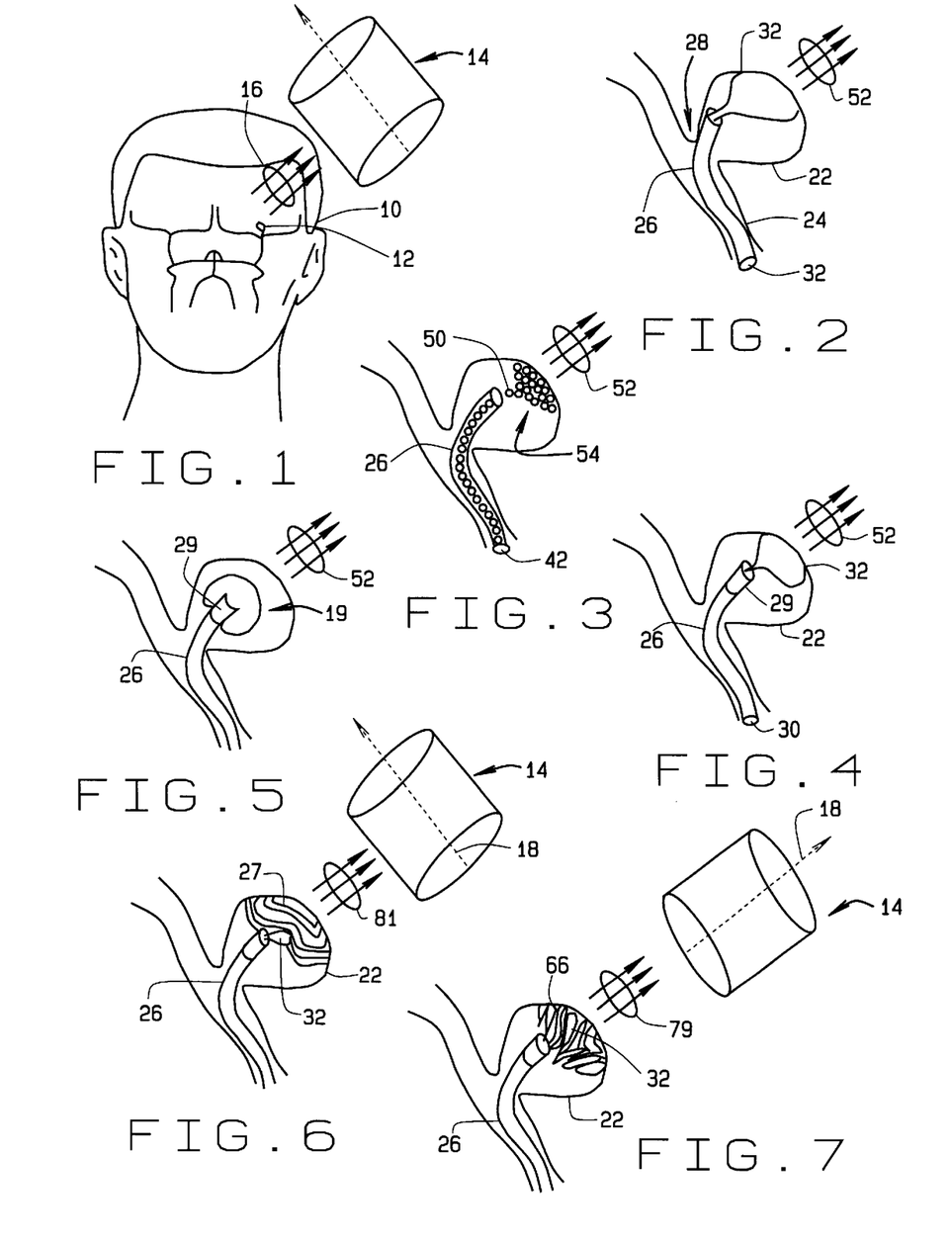
FIG. 1 is a schematic illustration of the overall context of the invention.
FIG. 2 is a schematic representation of ferro-fluid delivery in an aneurysm treatment procedure.
FIG. 3 is a schematic representation of macroscopic magnetic device delivery in an aneurysm treatment procedure.
FIG. 4 is a schematic representation of ferro-fluid delivery in an aneurysm treatment procedure.
FIG. 5 is a schematic representation of ferro-fluid delivery in an aneurysm treatment procedure.
FIG. 6 is a schematic representation of ferro-fluid delivery with transverse gradient in an aneurysm treatment procedure.
FIG. 7 is a schematic representation of ferro-fluid delivery with axial gradient in an aneurysm treatment procedure.

FIG. 1 represents a schematic illustration of a patient 10 undergoing a minimally invasive procedure to treat an aneurysm 12 using the methods and devices of this invention. The patient's head located near a magnet system 14. The magnet system 14 is controlled by the physician to generate and apply a magnetic field 16 at the treatment site.

The externally applied magnetic fields are described and shown schematically herein but other incorporated references describe these magnet systems in great detail. For example, the incorporated reference describes a suitable magnet system, which could be used to apply the magnetic field and to also image the magnetic device in the body. However, for purposes of this disclosure, the primary purpose of the magnet system 14 is to exert a well-defined and controlled magnetic field and magnetic gradient at the treatment site. Throughout the schematic illustrations, directional arrows are identified with labeling to indicate the preferred type of magnetic field and/or gradient for the magnetic device under control. These directional arrows are identified as a magnetic field 20, general gradient 52, axial gradient 79 and transverse gradient 81. These reference numerals are used throughout to identify these magnetic properties. Generally, the direction of the resultant attractive force generated by applied magnet is indicated in the figures by the direction of the arrow indicating the external magnetic field. The term general gradient 52 is used where the magnetic field direction with respect to the magnetic gradient direction is relatively unimportant for the process being described.

When the magnet system 14 is positioned with axis 18 parallel to the tractive forces, as seen in FIG. 7, the configuration may be referred to as an "axial" gradient 79. When the position of magnet system 14 with the axis 18 is perpendicular to the tractive forces as seen in FIG. 6 the configuration may be called a "transverse" gradient 81. In general, the control of the forces can be achieved either mechanically by moving the magnet system 14 with respect to the patient 10 or electrically by adjusting the currents in an electromagnet. For example, an axial field can be converted to a transverse field by rotation and translation of the magnet with respect to the position of the patient as seen in FIG. 1.

FIG. 2 shows an enlarged view of a portion of the vasculature of a patient containing an aneurysm 22. In practice, the physician will gain access to the vessel 24 and pass a catheter 26 through an introducer into the patient's vasculature. The catheter 26 will then be navigated using conventional guidewire techniques or under magnetic control as set forth in the incorporated references, to the treatment site. The physician will position the catheter 26 in the "neck" 28 of the aneurysm 22 with or without the aid of the magnet system. With the distal tip 30 of a catheter device 26 located within the neck 28 of the aneurysm, the physician can inject a magnetic device 32 into the cavity. In general a syringe or push wire (not shown) is coupled to the lumen 32 of the catheter 26, and the magnetic device 32 is extruded from the lumen of the catheter by the syringe or push wire. In FIG. 2 the catheter 26 device does not have a distal magnetic tip. Therefore, in this instance, the external gradient 52 along with syringe pressure serves to "meter" the magnetic device into the aneurysm by the forces resulting from the exterior magnet without the influence of any local magnetic field. In this particular drawing, the magnetic device 32 is a so-called "ferro-fluid".

The ferro-fluid type of magnetic device 32 may take any one of numerous formulations. In general, the material will be sufficiently viscous to be deliverable at reasonable flow rates trough a small catheter lumen under the pressure of a physician operated syringe. It has been found that the ferro-fluids used in experiments stiffen under the application of an external field. This effect must be taken into account during formulation. Experimentation has been preformed with carbonyl iron compounds in a cyanoacrylate carrier. In this combination, the iron material is in particulate form and the cyanoacrylate acts as a glue to solidify the composite material in the aneurysm. It is likely that temperature activated and light activated glues may be combined with magnetic particles to improve the solidification of the ferro-fluid. It is also anticipated that other diluent materials may be added to the ferro-fluid to modify and enhance the delivery properties of the material. Therefore, in this context, ferro-fluid should be understood to encompass microscopic particulate material, which is combined with a binder or glue agent which causes the ferrofluid to congeal into a solid mass after delivery. Both magnetic and magnitisable materials are operative and both cyanoacrylate and albumen based glues are operable. It is believed that the number of candidate materials for ferro-fluid is large and may include for example, hydrogels or copolymers mixed with the magnetically active particles. Throughout this specification, the term ferro-fluid is used to denote a material which is magnetically active and which is injected into the aneurysm or vascular defect. It should also be understood that other materials may be present in high concentrations to improve the delivery or reactive characteristics of the ferro-fluid. Embolization times and or solidification times of solidifying or adhesive agents vary considerably. Agents with shorter solidification times are most suitable. To improve the predictability of the solidification time, an agent could be mixed with the magnetic particles and activated with an external source. The external source could consist of ultra-violet light or radio frequency source. However, this method is not limited to a particular source used to activate the agent.

The ferro-fluid embodiments illustrated in FIGS. 2, 4, 5, 6, 7, have microscopic magnetic particulate. Larger particles may be used as well but the geometry of the occlusion process differs from that associated with smaller particles as discussed in connection with FIG. 3.

FIG. 3 shows a catheter 26 device for delivering discrete magnetic objects or particles typified by particle 50. The discrete objects may be as large as the catheter lumen 42. These particles may be sequentially inserted into the aneurysm. An external magnetic field 52 attracts and groups the individual objects, causing a single solid object 54 to form. Retention of the solid object 54 type of magnetic device, in the aneurysm reduces or prohibits blood flow through the aneurysm, causing it to clot. The shape of the magnetic objects can be spherical as shown or they may be cylindrical. However, many other shapes that are easily passed through a catheter device could be used as well. These magnetic devices may be coated with an adhesive forming a large particulate ferro-fluid. Given the relatively large volume of each device, the distribution of magnetic material may be non-uniform in the particle. Alternatively, the magnetic portion of the device may be concentrated and symmetrically placed. For example, the magnetic portion may be a small sphere of Hiperco coated with a thick layer of hydrogel or the like. For use in treating AVMs as seen in FIG. 17 the magnetic devices may have a coating such as polyvinyl alcohol (PVA) enclosing a magnetically active material such as magnetite or Hiperco.

Figure 17:
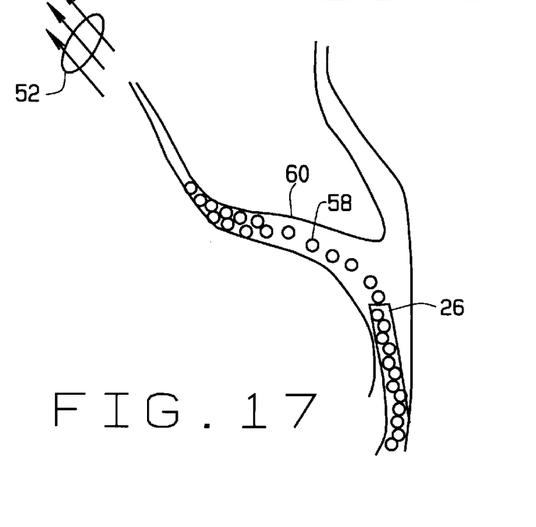
FIG. 17 is a schematic representation of magnetic object delivery in an AVM treatment procedure.

FIG. 17 shows a catheter delivering PVA coated magnetic particles into an AVM 56. In this particular procedure, the magnet gradient 52 attracts the magnetic devices typified by particle 58 along a path that lodges the particle in the branch 60 selected by the physician. In this instance, the external magnetic gradient is used along with blood flow in the vessel to direct the magnetic devices to the desired branch after they have left the distal tip of the catheter 26.

FIG. 4 shows another instance of a ferro-fluid type of magnetic device 32 used to fill an aneurysm 22, under the influence of an external magnetic gradient 52. However, in this instance the catheter body 26 includes a magnetically active distal tip 29. This tip 29 may be the most distal segment of the catheter body or it may be near the distal tip. In either event, the magnet or magnetic material 29 serves to constrict and control the flow of ferro-fluid out of the lumen 30. In this procedure, the flow of blood around the interior of the aneurysm is insufficient to overcome the tractive force holding the magnetic device 32 in the cavity and there is little risk of the material escaping from the cavity. Depending upon the glue or adhesive system used to prepare the ferrofluid, the external magnet remains on and in position long enough to allow the ferro-fluid to "set up" and become a solid mass. Once the ferro-fluid material has set, the magnet may be removed.

FIG. 5 shows a catheter device 26 similar to that of FIG. 4 but the relationship between the magnetic forces differs. In this embodiment the magnet structure 29 at the tip is relatively stronger than the applied force. In this situation the external magnetic field is "weaker" than the magnetic gradient 52 as in FIG. 4. In this instance, the ferro-fluid 32 is attracted to the distal magnetic tip structure 29 and forms a bloom 19 around the tip. The catheter would remain in place until the ferro-fluid 32 forms a solid or adheres to the aneurysm wall. Using this method, it may be important to ensure that the ferro-fluid does not bond or adhere to the catheter tip. However, other methods could be incorporated to leave the distal magnet in the aneurysm following the injection of the ferro-fluid surrounding the magnet. In addition, the externally applied magnetic gradient 52 could be eliminated with the distal magnet 29 supplying the entire attractive force to keep the ferro-fluid within the aneurysm.

FIG. 6 illustrates the application of a transverse gradient 81 to the ferro-fluid 32 as it exits the catheter 26. In this instance, the magnetic field and the magnetic gradient are perpendicular resulting in a force, which tends to cause the ferro-fluid to form layers or lamella in the aneurysm 22. With the application of a transverse gradient 81 at the aneurysm, the ferro-fluid 32 forms into structured layers or lamella as typified by layer 27. In this instance, the layers, typified by layer 27, adhere to one another and align with the field of the external magnet. It is preferred to align the layers perpendicular to the neck of the aneurysm to sufficiently "pack" the aneurysm and to prevent the material from forming in the nearby vessel branch.

FIG. 7 illustrates the application of an axial gradient 79 to the ferro-fluid 32 as it exits the catheter 26. In this instance, the magnetic field and the magnetic gradient are parallel resulting in a force, which tends to cause the ferro-fluid to form peaks in the aneurysm 22. These appear as columns of closely spaced structures in the aneurysm typified by structure 66. Utilizing this method, a smaller volume of ferro-fluid can effectively reduce the blood flow into the aneurysm, causing a clot to form. The choice between the use of a "transverse" or "axial" gradient or some intermediate field is essentially a medical choice driven in part by the volume and shape of the aneurysm as well as the relative size of the "neck".

Figure 18:
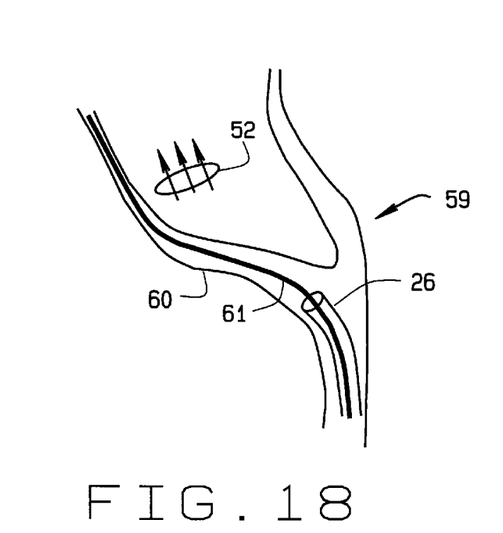
FIG. 18 is a schematic representation of ferro-fluid delivery in an AVM treatment procedure.

FIG. 18 illustrates the use of a ferro-fluid type magnetic device 61 to treat an AVM 59. In this instance, the catheter 26 ejects a stream of ferro-fluid that is magnetically solidified forming a "toothpaste-like string" 61 which is advanced into the branch 60 where occlusion occurs. Once again the external field 52 can both direct and retain the ferro-fluid in a structured form while the adhesive material in the ferro-fluid composition sets up. Using this approach, an adhesive or polymer agent can be administered to the AVM without concern for the agent passing through the AVM and appearing in the general circulation.

The various ferro-fluid embodiments allow the physician to fill the vascular defect with a selectable amount of material that typically adheres to or conforms to the shape of the defect. That is, the granularity of the particulate is so fine that an excellent match between the shape of the defect and the shape of the treatment device can be achieved, along with a matching of volume as well. Coil systems do not possess this feature.

Figure 9:
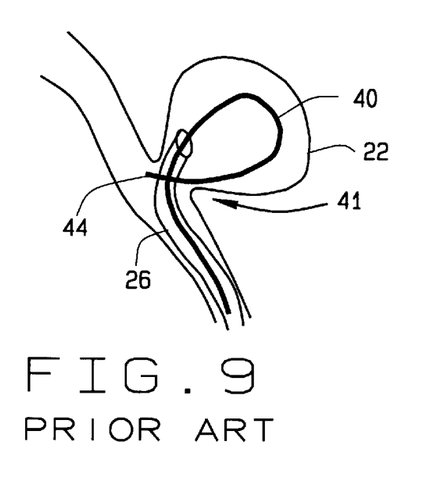
FIG. 9 is a schematic representation of a complication during a standard aneurysm treatment procedure, and represents a Prior Art problem addressed by the invention.

FIG. 9 shows a problem present with prior-art, coil placement systems. It is common to have the coil 40 curl up and pass out of the neck 41 of the aneurysm 22 reentering the vasculature near the neck as seen by the position of the distal tip 44 of the coil 40. In this prior-art system, the physician will retract the coil 40 back into the catheter 26 and try to twist and reposition the catheter to prevent the reoccurrence of the event. The physician may also retract and replace the coil with a smaller diameter coil to enable proper coil delivery.

Figure 8:
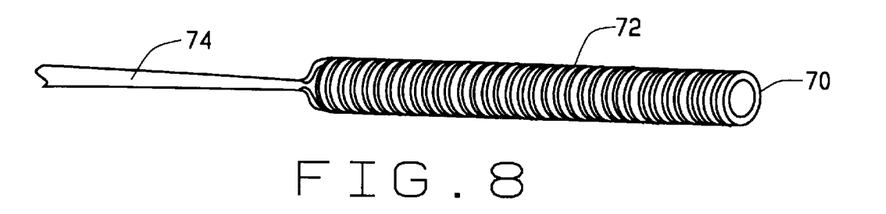
FIG. 8 is a schematic representation of a magnetically steerable coil for aneurysm treatment.

FIG. 8 shows a coil type magnetic device that includes a magnetic or magnetically active tip structure 70 mounted on a coil 72. The coil may be platinum or another non-magnetic material. The coil is temporarily attached to a push wire 74. The push wire is used to advance the coil from the distal opening of a catheter to retrieve the coil back into the catheter. This form of magnetic device may be biased into a straight form as seen in the drawing or it may be biased into a preformed curve shape, which may be advantageously used to direct the device into aneurysms. Typically coils are biased into curvilinear shapes to assist in placement. This particular construction is well suited for magnetically winding a coil using an external magnetic field in aneurysms.

Figure 10:
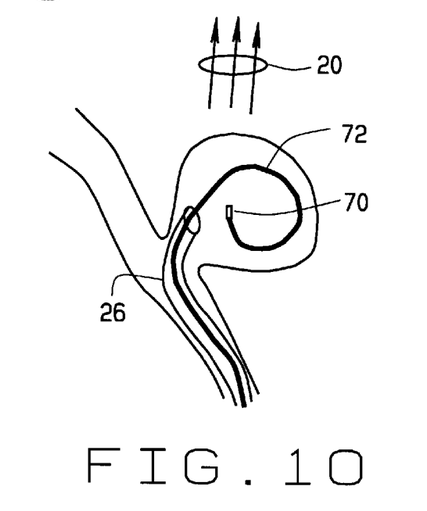
FIG. 10 is a schematic representation of magnetic coil winding in an aneurysm treatment procedure.

FIG. 10 shows a magnetic device of FIG. 8 being pushed out of a catheter 26. The externally applied field 20 aligns the tip of the coil towards the center of the aneurysm, permitting the coil to be tightly wound into the aneurysm. This is shown in the drawing by the decreasing radius of the coil. This feature overcomes the "first coil" problem explained in connection with FIG. 9.

Figure 11:
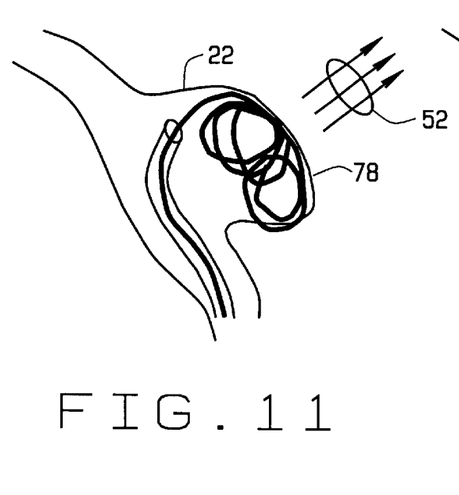
FIG. 11 is a schematic representation of magnetically holding coils in an aneurysm treatment procedure.

FIG. 11 shows a method for magnetically holding coils in an aneurysm. This magnetic coil device 78, is formed from a magnetiseable material such as "Hiperco" or 400 series Stainless Steel in a form similar to the coil 72 of FIG. 8. This magnetic device 78 is held in the dome of the aneurysm by the magnetic gradient 52 of the applied field. In this instance, the wire of the coil has an affinity for itself and the complex form taken by the wire is three-dimensional and essentially fills the entire dome of the aneurysm 22. This method for magnetically holding coils within an aneurysm is particularly useful for treating aneurysms with large necks. Standard coils cannot be held within large neck aneurysms without applying a balloon to close off the neck. The balloon method presents a greater risk that can be obviated by the use of magnetically held coils. Once a number of coils are inserted into the aneurysm, the interlocked coils are mechanically maintained in the aneurysm without the need for a sustained magnetic gradient. It is important to note that this approach allows for the reconstruction of a vascular defect that may not be treatable with more conventional coiling and clipping techniques.

Figure 12:
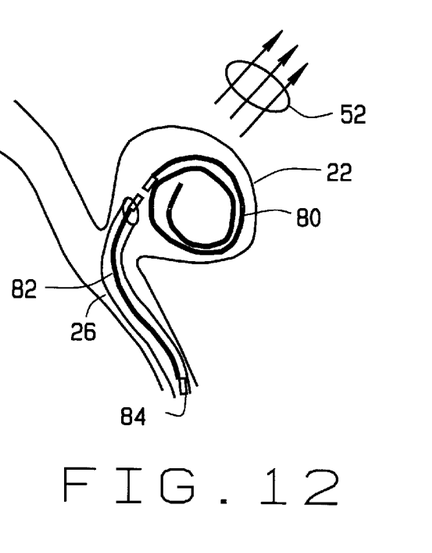
FIG. 12 is a schematic representation of magnetically releasing coils in an aneurysm treatment procedure.

FIG. 12 shows a number of coil type magnetic devices used to treat an aneurysm 22. Coil 84 and coil 82 are within the catheter 26 while coil 80 has been detached into the aneurysm 22. Winding multiple coils allows for the use of preloaded fixed length devices. The application of an external gradient creates sufficient force 52 that the coil 80 is detached from the remaining sequence of coils by overcoming the force of attraction between the magnet on coil 83 on coil 80. Using this approach, a number of coils can be inserted into an aneurysm and individually released without the need to load a new coil with push wire into the catheter between each coil release. This process speeds the treatment of a vascular defect.

Figure 13:
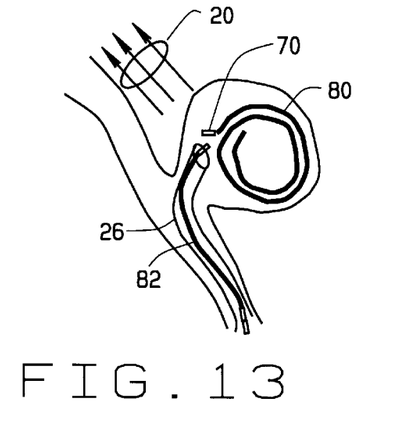
FIG. 13 is a schematic representation of magnetically releasing coils in an aneurysm treatment procedure.

FIG. 13 shows a use of a torque by an external magnetic field to detach a coil 80 from the complementary coil 82. In this instance the catheter 26 retains the coil 82 and resists the motion induced in magnet 70 by the external field 20.

Figure 14:
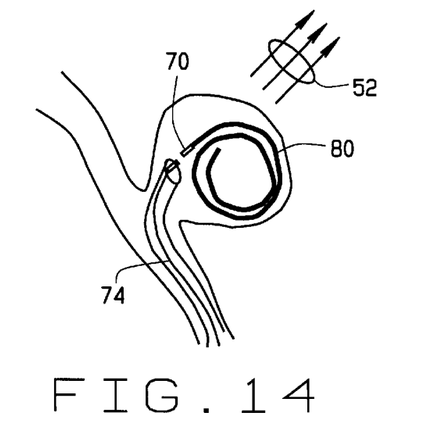
FIG. 14 is a schematic representation of magnetically releasing coils in an aneurysm treatment procedure.

FIG. 14 shows a use of a magnetic gradient 52 to detach a coil 80 from the push wire 74. In this instance, the catheter 26 retains the coil 80 allowing the coupling force between magnet 70 and the push wire to be overcome by the gradient force 52 from the externally applied magnet.

Figure 15:
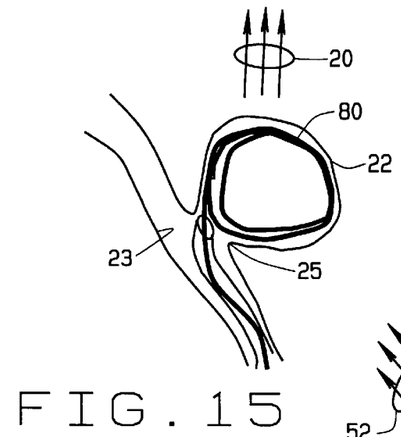
FIG. 15 is a schematic representation of magnetic coil winding in an aneurysm treatment procedure.
Figure 16:
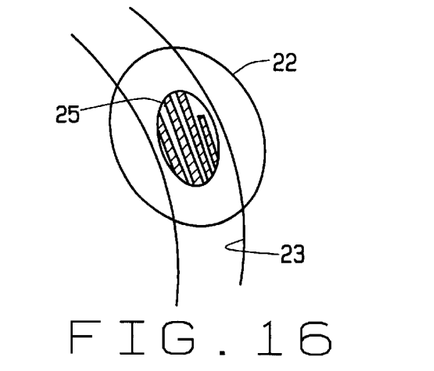
FIG. 16 is a schematic representation of magnetic coil winding across the neck in an aneurysm treatment procedure.

FIG. 15 and FIG. 16 should be considered together as they illustrate the same procedure. In FIG. 15 a coil 80 is magnetically wound, crossing the neck 25 of the aneurysm several times. In FIG. 16, the view shows the cross-section of the neck 25 and aneurysm 22 as seen from inside the vessel 23. By placing one large loop in the aneurysm crossing the neck several times, the neck 25 is almost completely blocked off without "filling" the aneurysm in the conventional sense. It is believed that the reduction in blood flow into and out of the aneurysm due to this blockage will be sufficient to encourage the formation of an embolism without the necessity of completely filling the aneurysm with coils.

Figure 19:
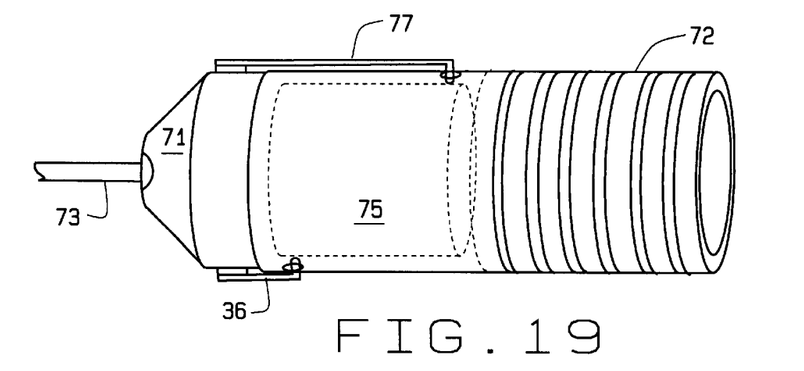
FIG. 19 is a schematic diagram of a magnetically actuated release mechanism (non-actuated state)

FIG. 19 is a schematic view of a magnetically actuated detachment mechanism used to uncouple a magnetic device, such as coil 72, from a push wire 73. In this magnetic device, the push wire terminates in a cap 71 that is positioned near a first cantilevered latch arm 77 and a second latch arm 36 near the coil 72. A magnet 75 is positioned for rotational motion near the cap 71.

Figure 20:
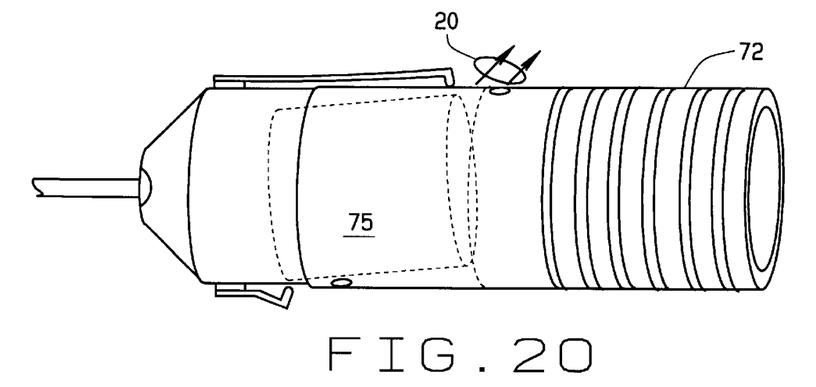
FIG. 20 is a schematic diagram of a magnetically actuated release mechanism (actuated state); and, FIG. 21 is a schematic diagram of a ferro-fluid magnetic device activated by an external energy source.

FIG. 20 shows an external magnetic field indicated by arrows 20 acting on the magnet 75 tilting it to force the latch arms to expand releasing the coil 72. Although this mechanism is shown on a push wire to coil connection, it can be used on a sequence of coils as seen in FIG. 12.

Figure 21:
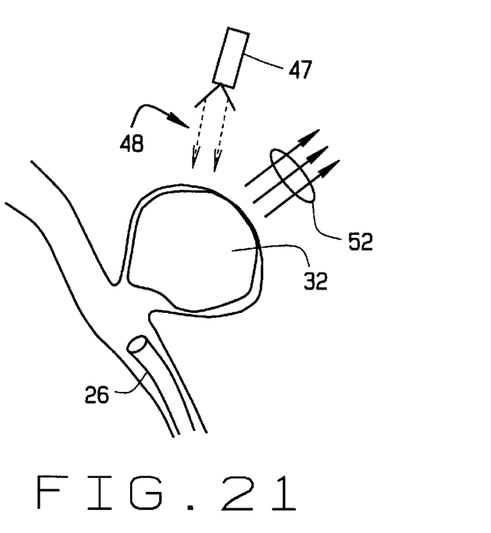

FIG. 21 shows an external energy source 47 delivering energy 48 to a ferro-fluid 32. The gradient 52 retains the bolus of ferro-fluid in the aneurysm 22 while the energy 48 catalyses the reaction to solidify the ferro fluid 32. The catheter 26 is retracted so that it does not adhere to the ferrro-fluid.

It should be apparent that many modifications to the devices and delivery system are within the scope of this disclosure, and that these changes can be made without departing from the scope of the claims.

What is claimed is:

1. A magnetically actuated latching device for releasing a device within a vascular defect consisting of a magnet contained within a cylinder with leaf springs attached to the cylinder such that when the magnet is torqued within the cylinder, the leaf springs are expanded to enable the device to be released.

2. The device in claim 1, whereby the vascular defect is an aneurysm and the device to be released is an aneurysm coil.

3. A method of treating an aneurysm comprising the steps of:

placing a macroscopic magnetic particle generating a local magnetic field and gradient in the aneurysm; and ejecting a ferro-fluid into the aneurysm surrounding said macroscopic magnetic particle, whereby said local magnetic field and gradient of said particle shapes and positions said ferro-fluid in said aneurysm.

4. A method of treating a vascular defect at a treatment site in a patient's body with a magnetic object of the type including a magnetic material, the method comprising the steps of:

a) navigating a catheter, having a lumen therein opening near a distal tip of the catheter, through vasculature in the patient's body to the treatment site;

b) generating a magnetic field at said treatment site within the patient's body from a source magnet located outside of the patient's body; and c) ejecting the magnetic object from the opening of the lumen of said catheter, the magnetic object entering the vascular defect and being retained in the vascular defect by the gradient of said magnetic field.

5. The method of claim 4 wherein the magnetic field has a gradient at the treatment site oriented with respect to the magnetic field to hold said magnetic object at said treatment site with the magnetic object in contact with a wall of the vascular defect.

6. The method of claim 4 wherein said vascular defect is an aneurysm.

7. The method of claim 4 wherein said vascular defect is anateriovenous malformation.

8. The method of claim 4 wherein the magnetic object is a magnetic mixture, the magnetic field holding and shaping the magnetic mixture within the vascular defect while the magnetic mixture is ejected into the vascular defect, the shape being determined by the presence of the magnetic field and a magnetic gradient acting on the magnetic mixture within the vascular defect independent of blood flow in the vascular defect.

9. The method of claim 4 wherein the magnetic object is made of a permeable magnetic material.

10. The method of claim 4 wherein the magnetic object is made of a permanent magnetic material.

11. The method of claim 4 wherein the magnetic object comprises a magnetic particle surrounded by a polyvinyl alcohol shell.

12. A method of treating a vascular defect at a treatment site in a patient's body with a magnetic object of the type including a magnetic material, the method comprising the steps of:

a) navigating a catheter, having a lumen therein opening near a distal tip of the catheter, through vasculature in the patient's body to the treatment site;

b) generating a magnetic field at said treatment site within the patient's body from a source magnet located outside of the patient's body; and c) ejecting a coil made from a permeable magnetic material from the opening of the lumen of said catheter, the magnetic object entering the vascular defect and being retained in the vascular defect by the gradient of said magnetic field.

13. The method of claim 12 wherein the coil has the first and second end with at least one end of the coil comprised of a magnetically permeable material.

14. The method of claim 13 wherein the step of ejecting a magnetic object from said lumen of said catheter is repeated for each of a plurality of magnetic coils; whereby a plurality of coils are sequentially inserted into the vascular defect and magnetically held in place until a sufficient number of coils have been inserted to form a self-retaining mass in the vascular defect.

15. A method of treating an aneurysm that opens to a blood vessel through a neck, the method comprising:

a) navigating a catheter, having a lumen therein opening near the distal tip of the catheter, through vasculature in the patient's body and into the neck of the aneurysm;

b) ejecting a coil, having a proximal end and a distal end, and a magnet on the proximal end, out the distal end of the lumen by pushing the coil with a guide inside the lumen of the catheter, the guide having a distal end and a magnet on the distal end for magnetically engaging the magnet on the proximal end of the coil;

c) applying a magnetic force to a juncture of the proximal end of the coil and the distal end of the guide to break the magnetic engagement between the coil and the guide to release the coil into the aneurysm.

16. A method of treating a vascular defect at a treatment site in a patient's body with a magnetic mixture of the type including magnetic particles and an agent that cures into a solid mass, the method comprising the steps of:

a) navigating a catheter, having a lumen therein opening near a distal tip of the catheter and a magnetically responsive element near the distal tip of the catheter, through vasculature to said treatment site;

b) generating a magnetic field at said treatment site within the patient's body from a source magnet located outside of the patient's body; and c) ejecting the magnetic mixture from the lumen of the catheter, with the magnetic field at the treatment site aligned to draw the magnetic mixture into, and hold the magnetic mixture within, the vascular defect.

17. The method of claim 16 wherein the magnetic mixture for treating the vascular defect comprises magnetic particles combined with a material selected from biocompatible glues, absorbable plastic materials, hydrogels, polymers, and copolymers.

18. The method of claim 17 wherein the magnetic mixture for treating the vascular defect consists of a non-adhesive copolymer that can be ejected from the catheter as the magnetic mixture is shaped by the magnetic field acting on the magnetic particles distributed throughout the copolymer.

19. The method of claim 18 wherein said vascular defect is an aneurysm.

20. The method of claim 18 wherein the vascular defect is anateriovenous malformation, and wherein the magnetic mixture is temporarily magnetically rigidified while it is ejected from the lumen of the catheter into the arteriovenous malformation, by the application of the magnetic field, to facilitate navigation of the magnetic mixture into the arteriovenous malformation.

21. A method of treating a vascular defect at a treatment site in a patient's body with a magnetic mixture of the type including magnetic particles and an agent that cures into a solid mass, the method comprising the steps of:

a) navigating a catheter, having a lumen therein opening near a distal tip of the catheter and a magnetically responsive element near the distal tip of the catheter, through vasculature, to said treatment site;

b) generating a magnetic field at said treatment site within a patient's body from a source magnetic located outside of the patient's body; and c) ejecting the magnetic mixture, comprising magnetic particles combined with a non-adhesive material selected from biocompatible glues, absorbable plastic materials, hydrogels, polymers, and copolymers, from the lumen of the catheter, with the magnetic field at the treatment site aligned to draw the magnetic mixture into, shape the magnetic mixture by the magnetic field acting on the magnetic particles distributed throughout the material, and hold the magnetic mixture within, the vascular defect, the applied magnetic field orienting the catheter while the magnetic mixture is ejected into the vascular defect, and a magnetic gradient of the applied magnetic field drawing the ejected magnetic mixtures into the vascular defect.

22. The method of claim 18 wherein the distal tip of catheter is navigated into the vascular defect, and wherein the magnetically responsive element at the distal tip of the catheter assists in the retention of the magnetic mixture in the vascular defect.

23. The method of claim 18 wherein the direction of the applied magnetic field at the treatment site is transverse with the direction of the magnetic gradient of the applied magnetic field to layer and hold the magnetic mixture within the vascular defect.

24. The method of claim 18 wherein the direction of the applied magnetic field at the treatment site is axially aligned with the direction of the magnetic gradient of the applied magnetic field to form the magnetic mixture into columns within the vascular defect.

25. The method of claim 18 wherein the magnetically responsive element is comprised of a magnetic permeable material.

26. The method of claim 18 wherein the magnetically responsive element is comprised of a permanent magnet.

27. A method of treating a vascular defect at a treatment site in a patient's body with a magnetic mixture of the type including magnetic particles and an agent that cures into a solid mass, the method comprising the steps of:

a) navigating a catheter, having a lumen therein opening near a distal tip of the catheter and a magnetically responsive element near the distal tip of the catheter, through vasculature, to said treatment site;

b) generating a magnetic field at said treatment site within a patient's body from a source magnetic located outside of the patient's body; and c) ejecting the magnetic mixture, comprising magnetic particles combined with a non-adhesive material selected from biocompatible glues, absorbable plastic materials, hydrogels, polymers, and copolymers, from the lumen of the catheter, with the magnetic field at the treatment site aligned to draw the magnetic mixture into, shape the magnetic mixture by the magnetic field acting on the magnetic particles distributed throughout the material, and hold the magnetic mixture within, the vascular defect, while reducing the strength of the applied magnetic field as the magnetic mixture is ejected.

28. The method of claim 27 wherein the strength of the applied magnetic field is reduced by increasing a distance between the source magnet and the treatment site.

29. The method of claim 27 wherein the source magnet is at least one electromagnet, and wherein the strength of the applied magnetic field is reduced by decreasing a current applied to the at least one electromagnet.

30. A method of treating a vascular defect within the patient's body comprising the steps of:

a) navigating a device having an opening near the distal tip of the device, through the vasculature in a patent to the vascular defect;

b) generating a magnetic field within the patient's body at the vascular defect from a source magnet located outside of the patient's body;

c) ejecting a flowable magnetic mixture that is curable to a solid form from the opening at the distal tip of the device whereby the flowable magnetic mixture enters the vascular defect and is retained in the vascular defect by the magnetic field; and d) applying a curative agent to the flowable magnetic mixture to cure the flowable magnetic mixture within the vascular defect.

31. The method of claim 30 wherein the magnetic mixture for treating the vascular defect comprises magnetic particles combined with a material from the group at least one of the following: glues, absorbable plastic materials, hydrogels, polymers, and copolymers, which is curable upon the application of a curative agent to form a solid.

32. The method of claim 31 wherein the vascular defect is an aneurysm.

33. The method of claim 31 wherein the vascular defect is anarteriovenous malformation.

34. The method of claim 31 wherein the curative agent which cures the flowable magnetic mixture is a chemical.

35. The method of claim 31 wherein the curative agent which cures the flowable magnetic mixture is magnetic energy.

36. The method of generating an external magnetic field to hold a magnetic mixture in an aneurysm comprising the steps of:

a) acquiring images of an aneurysm site in a patient from different perspectives of a patient volume using bi-planer fluoroscopy;

b) navigating a catheter having a lumen therein opening near a distal tip of the catheter and a magnetically responsive element near the distal end of the catheter, through the vasculature of patient to the aneurysm site;

c) indicating one at least two images where the magnetic mixture will be ejected;

d) using an external magnet system along an axis of the aneurysm at a distance which provides sufficient, but not excessive magnetic field to hold the magnetic mixture in the aneurysm; and e) ejecting an embolic material containing a magnetic mixture from the lumen at the distal tip of the catheter whereby the embolic material enters the aneurysm and is retained in the aneurysm by the magnetic field generated by the magnetically responsive element.

37. A method for treating an aneurysm with a coil having first and second ends, and a magnet associated with the first end of the coil, the method comprising the steps of:

a) navigating a catheter having a lumen therein and an opening near a distal tip of the catheter, through vasculature to an aneurysm site;

b) pushing the coil from the lumen to first expose the first end of the coil from the opening;

c) pushing the coil from the lumen so that the second end of the coil extends slightly from the distal end of the catheter; and d) applying an external magnetic field to steer the magnet associated with the first end of the coil towards a center of the aneurysm to direct the coil to wind within the aneurysm as the coil is advanced into the aneurysm.

38. The method of claim 37 wherein a single coil is magnetically steered to optimally block the neck of the aneurysm as the coil is wound with the aneurysm.

39. An apparatus for releasing at least one coil from a catheter into a vascular defect, the apparatus comprising:

a catheter with an opening at a distal end of the catheter; and a releasing mechanism located in the catheter near the opening, the releasing mechanism being influenced by an applied magnetic field to uncouple the at least one coil from the releasing mechanism, the releasing mechanism ejecting the at least one coil from the opening into the vascular defect.

40. The device of claim 39 wherein the releasing mechanism comprises a push wire, the push wire advancing the at least one coil toward the opening of the catheter, where a magnetic gradient from an applied magnetic field can magnetically uncouples the at least one coil from the push wire to eject the at least one coil into the vascular defect.

41. The device of claim 39 wherein the releasing mechanism is comprised of a magnetically actuated latching mechanism, the magnetically actuated latching mechanism comprising latch arms operably connected to a magnetic permeable material, the latch arms having a hold position and a release position, the latch arms being actuated between the hold position and the release position by the magnetic permeable material, the hold position restraining the object with the mechanism and release position releasing the object from the mechanism into the vascular defect, the magnetic permeable material being influenced to actuate the latch arms by the magnetic gradient.

42. A method of treating an aneurysm comprising the steps of:

a) placing a macroscopic magnetic particle in the aneurysm; and b) ejecting a magnetic mixture into the aneurysm such that the magnetic mixture surrounds said macroscopic magnetic particle;

whereby a local magnetic field created by said macroscopic particle, shapes and positions said magnetic mixture in said aneurysm.

43. A biocompatible magnetic mixture which can be ejected through a standard microcatheter and held magnetically within a vascular defect, the biocompatible magnetic mixture comprised of:

a) a magnetic particulate between 1 mm and 10 mm in diameter, selected from the group consisting of iron, coated iron, carbonyl-iron, and iron carbon composites;

b) a polymer selected from the group consisting of cellulose acetate, polymerized methyl-methacrylate, or ethyl vinyl alcohol; and c) a solvent which dissolves the polymer selected from the group consisting of DMSO, acetone, and ethyl acetate;

whereby said magnetic particulate and polymer are homogeneously distributed throughout said solvent, which precipitates from the solution as the magnetic mixture is deposited into said vascular defect and as the magnetic mixture is held by an externally applied magnetic field.

44. A biocompatible magnetic mixture which can be delivered through a microcatheter and held magnetically within a vascular defect, the biocompatible magnetic mixture comprised of:

a) a magnetic particulate between 1 mm and 10 mm in diameter, selected from the group consisting of iron, coated iron, carbonyl-iron, and iron carbon composites;

b) a polymer selected from the group consisting of cellulose acetate, polymerized methyl-methacrylate, and ethyl vinyl alcohol;

c) an adhesive agent selected from the group consisting of cyanoacrylates;

d) a solvent for dissolving the polymer selected from the group consisting of DMS0, acetone, and ethyl acetate; and whereby said adhesive agent improves the cohesiveness and tissue attachment characteristics of the said magnetic mixture while magnetic particulate, adhesive agent and polymer are homogeneously distributed throughout said solvent, which precipitates from the solution as the magnetic mixture is deposited into said vascular defect and as the magnetic mixture is held by an externally applied magnetic field.

* * * * *